(12) United States Patent
Sami et al.

(10) Patent No.: US 9,289,199 B1
(45) Date of Patent: Mar. 22, 2016

(54) RETINAL EXAMINATION APPARATUS

(71) Applicants: David A. Sami, Los Angeles, CA (US); Arnold M. Heyman, Los Angeles, CA (US); Lawrence C. Kiliszewski, The Woodlands, TX (US)

(72) Inventors: David A. Sami, Los Angeles, CA (US); Arnold M. Heyman, Los Angeles, CA (US); Lawrence C. Kiliszewski, The Woodlands, TX (US)

(73) Assignee: Neotech Products, Inc., Valencia, CA (US)

( * ) Notice: Subject to any disclaimer, the term of this patent is extended or adjusted under 35 U.S.C. 154(b) by 121 days.

(21) Appl. No.: 13/999,051

(22) Filed: Jan. 9, 2014

(51) Int. Cl.
*A61B 1/32* (2006.01)
*A61B 17/02* (2006.01)

(52) U.S. Cl.
CPC .......... *A61B 17/0231* (2013.01); *A61B 17/0206* (2013.01)

(58) Field of Classification Search
CPC ................ A61B 17/0231; A61B 17/0206
USPC ................................. 600/184–246
See application file for complete search history.

(56) References Cited

U.S. PATENT DOCUMENTS

| | | | | |
|---|---|---|---|---|
| 1,375,445 A * | 4/1921 | Crossley | A61F 9/007 | 600/227 |
| 2,438,646 A * | 3/1948 | Pulliam | A61B 1/32 | 600/231 |
| 2,702,540 A * | 2/1955 | Debeh | A61B 17/0231 | 600/218 |
| 3,680,546 A * | 8/1972 | Asrican | A61B 1/07 | 385/117 |
| 4,037,589 A * | 7/1977 | McReynolds | A61B 17/0231 | 600/209 |
| 4,257,406 A * | 3/1981 | Schenk | A61B 17/0231 | 600/219 |
| 5,054,906 A * | 10/1991 | Lyons, Jr. | A61B 3/0008 | 351/205 |
| 5,088,472 A * | 2/1992 | Fakhrai | A61B 17/0206 | 600/214 |
| 5,163,419 A * | 11/1992 | Goldman | A61B 17/0231 | 600/206 |
| RE34,150 E * | 12/1992 | Santilli | A61B 17/0206 | 600/232 |
| 5,171,254 A * | 12/1992 | Sher | A61B 17/0231 | 600/232 |
| 5,341,798 A * | 8/1994 | Grounauer | A61B 17/0231 | 600/236 |
| 5,433,190 A * | 7/1995 | Sunalp | A61B 17/0231 | 600/236 |
| 5,441,040 A * | 8/1995 | Williams, Jr. | A61B 17/0231 | 600/236 |
| 5,556,417 A * | 9/1996 | Sher | A61B 17/0231 | 600/236 |
| 5,618,261 A * | 4/1997 | Nevyas | A61B 17/0231 | 600/236 |
| 5,695,492 A * | 12/1997 | Brown | A61B 17/0231 | 606/4 |
| 5,984,867 A * | 11/1999 | Deckman | A61B 17/0206 | 600/231 |
| 6,102,854 A * | 8/2000 | Cartier | A61B 1/32 | 600/210 |
| 6,113,536 A * | 9/2000 | Aboul-Hosn | A61B 17/0206 | 600/227 |
| 6,149,584 A * | 11/2000 | Raju | A61B 17/025 | 600/231 |
| 6,206,828 B1 * | 3/2001 | Wright | A61B 17/0206 | 600/232 |
| 6,283,912 B1 * | 9/2001 | Hu | A61B 17/02 | 600/210 |
| 6,283,913 B1 * | 9/2001 | Seibel | A61B 1/32 | 600/219 |
| 6,346,078 B1 * | 2/2002 | Ellman | A61B 17/0231 | 600/214 |
| 6,440,065 B1 * | 8/2002 | Hered | A61B 1/32 | 600/236 |
| 7,175,594 B2 * | 2/2007 | Foulkes | | 600/236 |
| 7,654,954 B1 * | 2/2010 | Phillips | A61B 17/0206 | 600/227 |
| 8,267,970 B2 * | 9/2012 | Serhan | A61B 17/7071 | 600/236 |
| 8,414,467 B2 * | 4/2013 | Finger | A61N 5/10 | 600/218 |
| 8,647,266 B2 * | 2/2014 | Beck | A61B 1/32 | 600/217 |
| 8,852,092 B1 * | 10/2014 | Davis et al. | A61B 1/32 | 600/236 |
| 8,915,848 B1 * | 12/2014 | Rixen | A61B 1/32 | 600/235 |
| 2002/0077532 A1 * | 6/2002 | Gannoe | A61B 17/02 | 600/232 |
| 2002/0095139 A1 * | 7/2002 | Keogh | A61B 17/0206 | 606/1 |
| 2002/0103421 A1 * | 8/2002 | Putrino | A61B 17/0231 | 600/236 |

(Continued)

*Primary Examiner* — Ellen C Hammond
*Assistant Examiner* — Stuart S Bray
(74) *Attorney, Agent, or Firm* — William W. Haefliger

(57) ABSTRACT

An eyelid speculum comprising a longitudinally Elongated support, first and second elongated members carried by the support to extend laterally, and eyelid positioning spoons carried by the members, at least one of the members having adjustable connection to the support to be selectively positioned relative to the other of the members whereby the spoons may be relatively adjustably positioned.

15 Claims, 4 Drawing Sheets

(56) References Cited

U.S. PATENT DOCUMENTS

| | | | |
|---|---|---|---|
| 2003/0065372 A1* | 4/2003 | D'Alessandro | A61B 17/0206 607/105 |
| 2003/0109885 A1* | 6/2003 | Tano | A61F 2/1662 606/107 |
| 2003/0171656 A1* | 9/2003 | Foulkes | A61B 1/00094 600/232 |
| 2004/0127773 A1* | 7/2004 | Douglas | A61B 17/02 600/227 |
| 2004/0220454 A1* | 11/2004 | Dalle | A61B 1/00142 600/186 |
| 2005/0115569 A1* | 6/2005 | Davis | A61B 17/0231 128/849 |
| 2005/0177028 A1* | 8/2005 | Royce | A61B 17/0293 600/210 |
| 2006/0052673 A1* | 3/2006 | Santilli | A61B 17/02 600/234 |
| 2007/0021656 A1* | 1/2007 | Martin | A61B 17/02 600/231 |
| 2007/0161865 A1* | 7/2007 | Fakhrai | A61B 17/0206 600/231 |
| 2007/0179345 A1* | 8/2007 | Santilli | A61B 17/0206 600/227 |
| 2008/0108879 A1* | 5/2008 | Brown | A61B 17/0231 600/236 |
| 2008/0177270 A1* | 7/2008 | Sorrenti | A61B 17/025 606/90 |
| 2009/0069634 A1* | 3/2009 | Larkin | A61B 1/303 600/222 |
| 2009/0076516 A1* | 3/2009 | Lowry | A61B 17/02 606/90 |
| 2009/0227845 A1* | 9/2009 | Lo | A61B 17/0206 600/212 |
| 2009/0227846 A1* | 9/2009 | Beck | A61B 1/32 600/236 |
| 2010/0268036 A1* | 10/2010 | Rothweiler | A61B 17/0206 600/214 |
| 2011/0066000 A1* | 3/2011 | Ibrahim | A61B 1/00154 600/205 |
| 2011/0077468 A1* | 3/2011 | Finger | A61B 1/32 600/236 |
| 2011/0098537 A1* | 4/2011 | Justis | A61B 17/0206 600/210 |
| 2011/0098538 A1* | 4/2011 | Terry | A61B 17/0231 600/236 |
| 2011/0112373 A1* | 5/2011 | Ainsworth | A61B 17/0218 600/207 |
| 2011/0172494 A1* | 7/2011 | Bass | A61B 17/0206 600/215 |
| 2011/0275903 A1* | 11/2011 | Shelton | A61B 17/0231 600/236 |
| 2012/0022335 A1* | 1/2012 | Assaker | A61B 17/0206 600/225 |
| 2012/0265213 A1* | 10/2012 | Beger | A61B 17/0206 606/102 |
| 2012/0316401 A1* | 12/2012 | Matsumura | A61B 17/0206 600/235 |
| 2012/0330106 A1* | 12/2012 | Wright | A61B 17/0206 600/218 |
| 2013/0072760 A1* | 3/2013 | Terry | A61B 17/0231 600/236 |
| 2013/0215383 A1* | 8/2013 | Siminou | A61B 3/14 351/206 |
| 2013/0237769 A1* | 9/2013 | Puskas | A61B 17/0206 600/232 |
| 2013/0267988 A1* | 10/2013 | Sussman | A61B 17/0231 606/198 |
| 2013/0317312 A1* | 11/2013 | Eastlack et al. | A61B 17/02 600/215 |
| 2013/0331656 A1* | 12/2013 | Knoepfle et al. | A61B 17/0231 600/236 |
| 2014/0031632 A1* | 1/2014 | Nakao | A61B 17/0206 600/206 |
| 2014/0031874 A1* | 1/2014 | Kucharzyk et al. | A61B 17/7076 606/279 |
| 2014/0066718 A1* | 3/2014 | Fiechter et al. | A61B 17/0206 600/214 |
| 2014/0142699 A1* | 5/2014 | Beger et al. | A61B 17/0206 623/17.11 |
| 2014/0221761 A1* | 8/2014 | Im | A61B 17/0206 600/214 |
| 2015/0018624 A1* | 1/2015 | Beck et al. | A61B 17/0206 600/206 |
| 2015/0065809 A1* | 3/2015 | Assia et al. | A61B 17/0231 600/217 |
| 2015/0305732 A1* | 10/2015 | Dahl | A61B 17/0206 600/214 |
| 2015/0320411 A1* | 11/2015 | Prywes | A61B 19/081 600/203 |

* cited by examiner

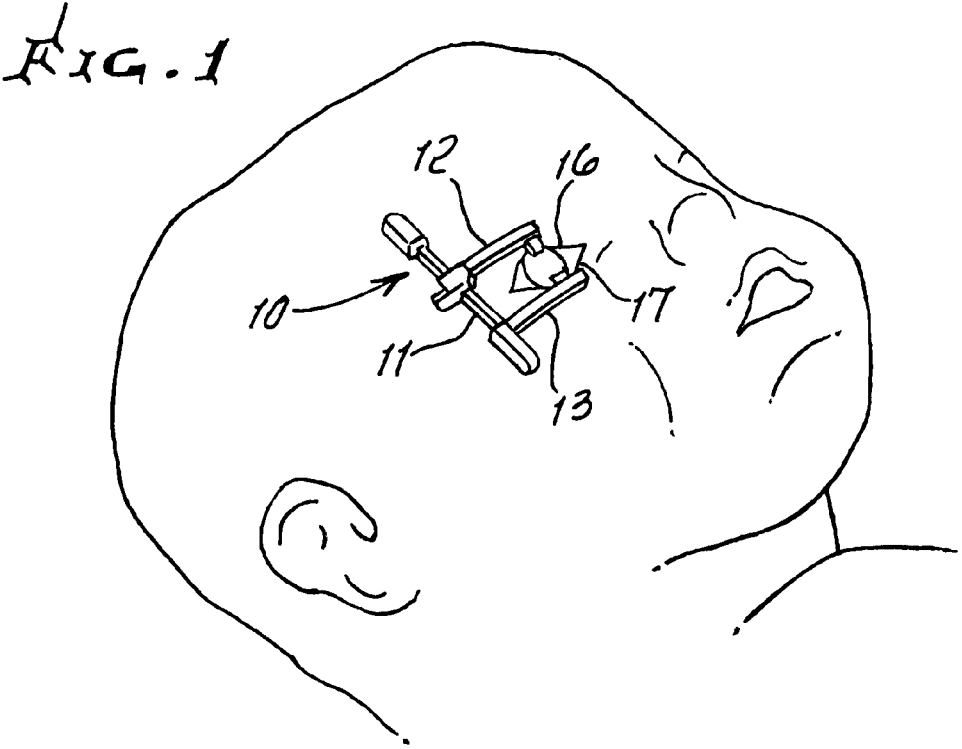
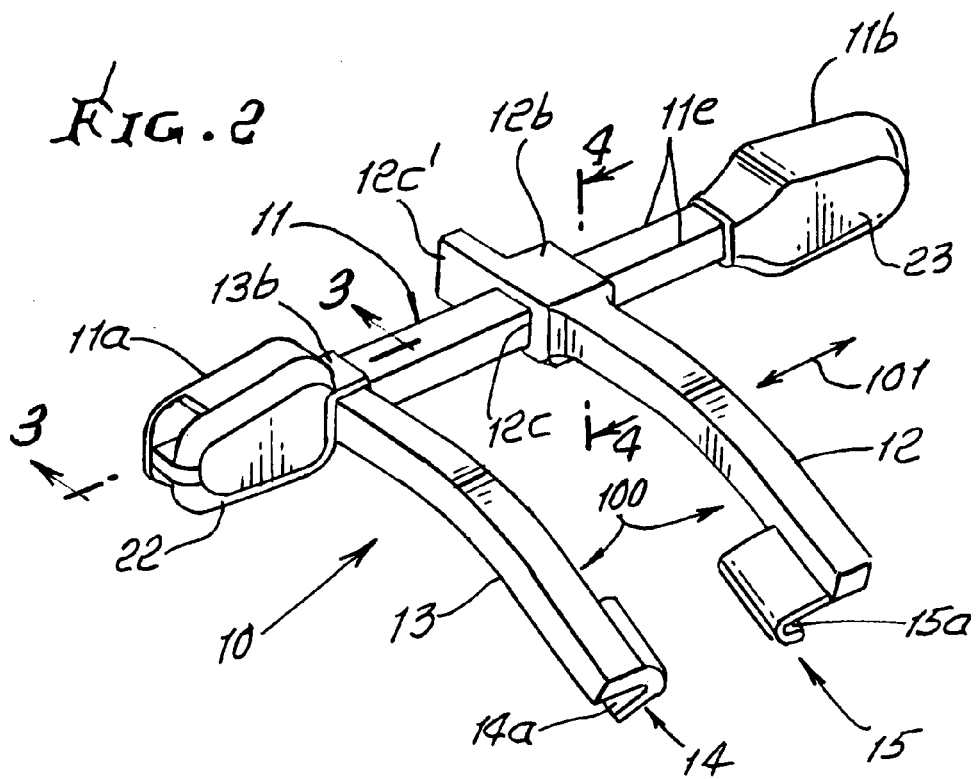

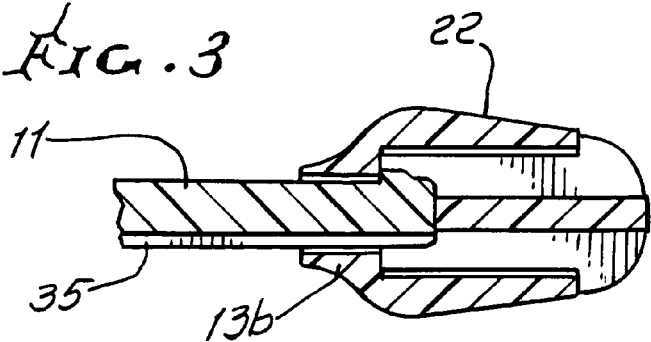
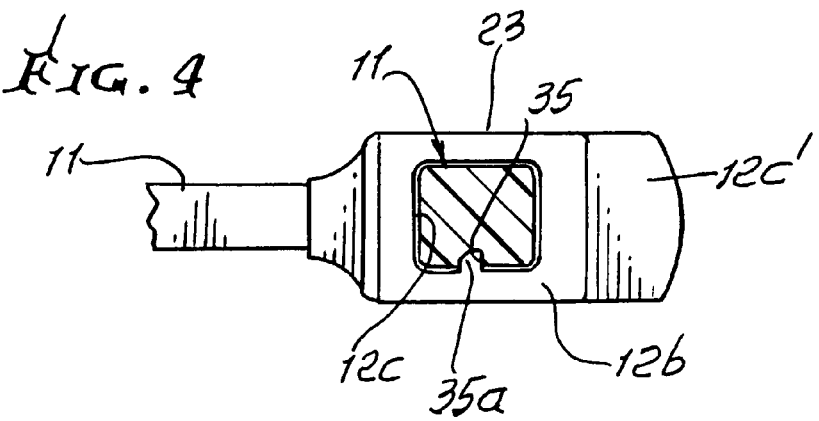
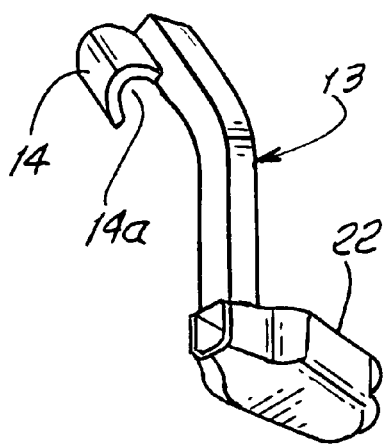
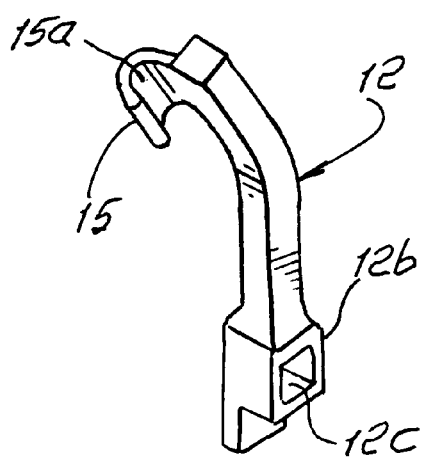

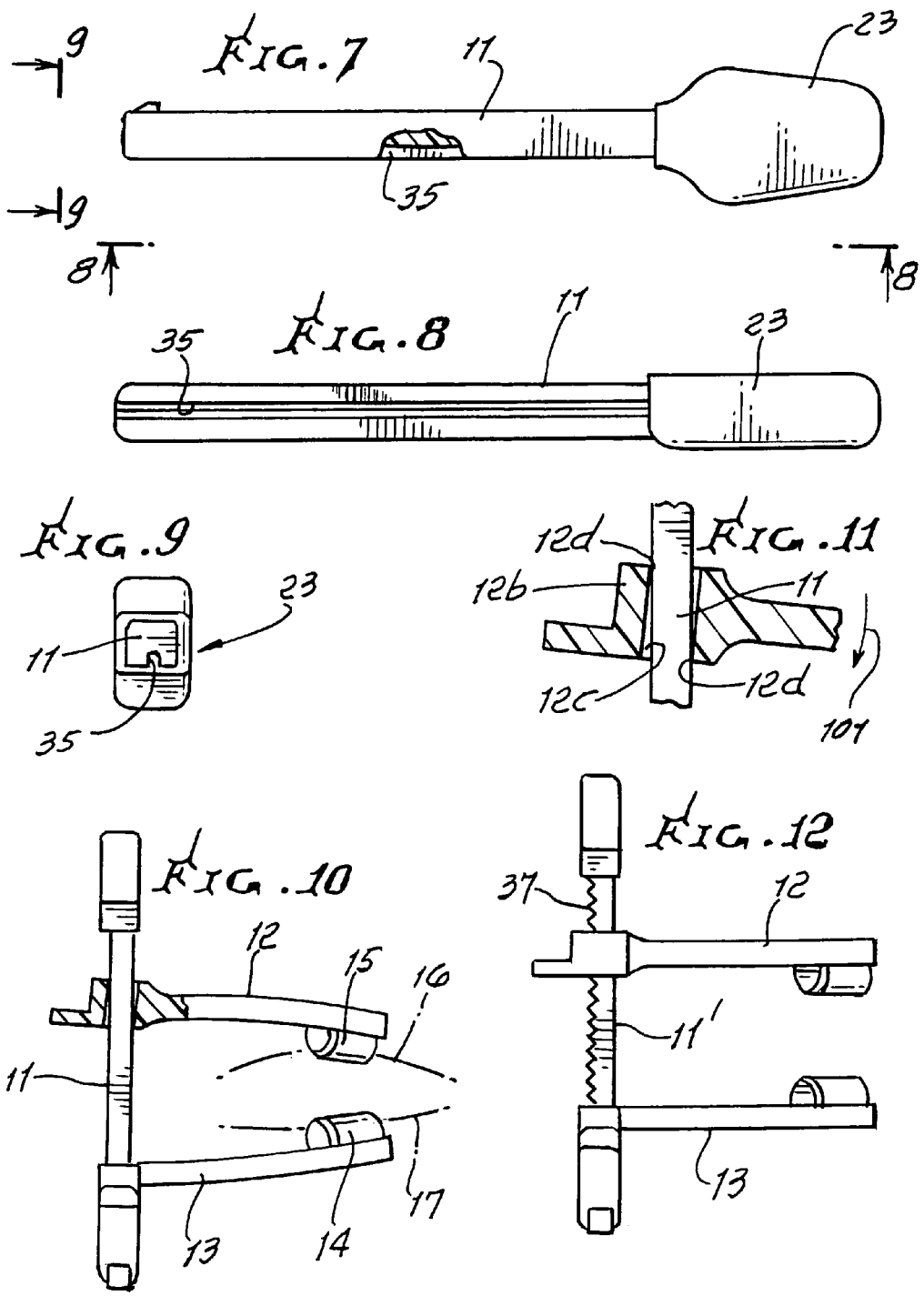

RETINAL EXAMINATION APPARATUS

BACKGROUND OF THE INVENTION

This invention relates generally to eyelid speculum apparatus operable to controllably retract a patient's eyelids; more specifically it concerns provision of two frames operatively interconnected to slide relation to one another, and in so doing serving to adjustably position eyelid retractors carried by the frames.

There is need for compact, easily adjustable, eyelid retractors, useful as during eye surgery and inspection. More particularly, there is need for eyelid speculum comprising:
  a) a longitudinally elongated support,
  b) first and second elongated members carried by the support to extend laterally, and eyelid positioning spoons carried by said members,
  c) at least one of the members having adjustable connection to the support to be selectively positioned relative to the other of said members whereby the spoons may be relatively adjustably positioned.

SUMMARY OF THE INVENTION

It is a major object of the invention to provide improved, easily manipulated, compact eyelid speculum meeting the above needs. Basically, apparatus meeting such need comprises the one member configured to have an end portion adjustably shiftable along the support, enabled by provision of a through opening to pass the support and defining a loose adjustable interconnection. That connection typically has interengagement surfaces on the one member and on the support providing limited rocking of the one member relative to the support and frictionally positioning. Such surfaces are positioned to enable selective rocking of said one member toward and away from the other member, to adjust the relative positioning of the spoons.

Another object is to provide:
  a) two frames operatively interconnected to slide relative to one another,
  b) and eyelid retractors carried by the frames.

Such frames typically have arms carrying the retractors, one retractor carried by one frame, and the other retractor carried by the other frame, for example via frame arms. The retractors or spoons typically have U-shaped curvature adapted to move apart as the frames relatively slide.

A further object includes provision of a tray that includes a container retaining the frames; the container having a transparent wall, and wherein the frames are retained in the container to be slidable directionally parallel to that wall.

These and other objects and advantages of the invention, as well as the details of an illustrative embodiment, will be more fully understood from the following specification and drawings, in which:

DRAWING DESCRIPTION

FIG. 1 is a perspective view of a speculum device, according to the invention, in use to retract an infant's eyelids;

FIG. 2 is an enlarged perspective view of a speculum device;

FIG. 3 is an enlarged section taken on lines 3-3 of FIG. 2;

FIG. 4 is an enlarged section taken on lines 4-4 of FIG. 2;

FIG. 5 is an enlarged perspective view of fixed structure carrying a retractor;

FIG. 6 is an enlarged perspective view of a slidable element carrying a retractor;

FIG. 7 is a side elevation view of support structure;

FIG. 8 is a view taken on lines 8-8 of FIG. 7;

FIG. 9 is an end view taken on lines 9-9 of FIG. 7.

FIG. 10 is an assembly view showing angulation of the slidable member of the speculum apparatus;

FIG. 11 is a further enlarged view showing edge engagement of the adjusted angulated member, to block sliding;

FIG. 12 is like FIG. 10, but shows use of a rack to facilitate adjustment; and

DETAILED DESCRIPTION

Figure 13:
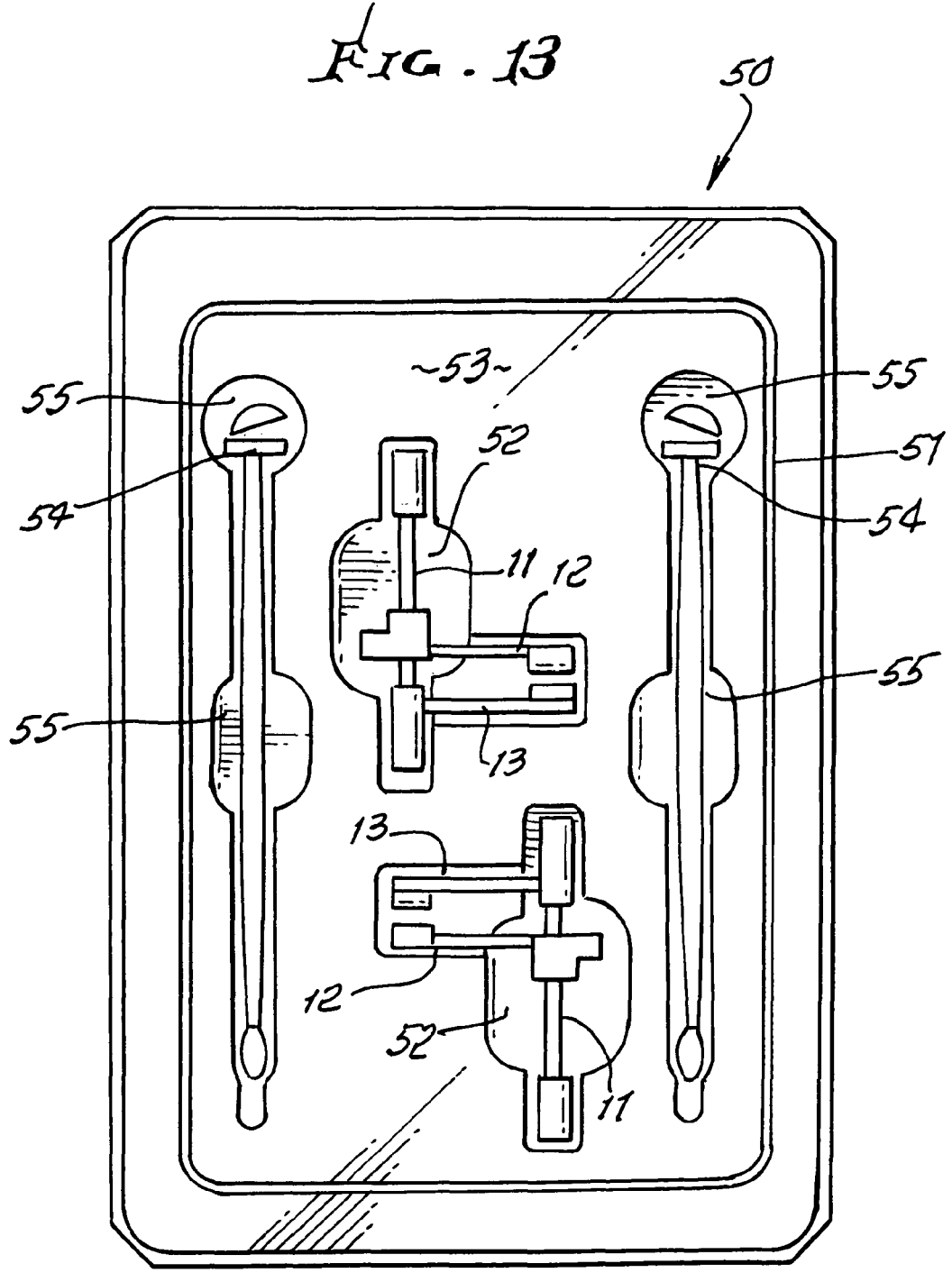
FIG. 13 shows a tray carrying two sets of such frames.

As shown in FIG. 2, the eyelid speculum 10 made of molded plastic material comprises a longitudinally elongated support 11 having a non-circular cross section, with edges 11e and enlarged ends 11a and 11b. First and second elongated members 12 and 13 are carried by the support 11 to extend laterally, and eyelid positioning spoons or retractors 14 and 15 are carried at ends 12b and 13b of the members. The spoons are carried to have U-shaped openings 14a and 15a facing away from one another, so as to receive eyelids 16 and 17 and to position them away from one another, as during eye surgery, as seen in FIG. 1.

Base 12b of member 12 is enlarged to form a non-circular opening 12c receiving support 11 to slide along that support, without rotating about the axis of the latter, from angularly and longitudinally positioning spoon 15 and eyelid 16 in selected spaced relation relative to spoon 14 and eyelid 17. Base 13b of laterally extending member 13 is fixed to support 11.

Opposite ends of the support 11 are enlarged at 22 and 23 and flattened to be easily manipulated by the user's fingers, to adjacent base 12b of member 12 lengthwise along the support to desired or needed spread positioning at 100 of the spoons. A flat projection 12c' from 12b extends at the opposite side of the support, from member 12, for finger manipulation to accomplish two functions:
  a) to adjust the desired spread position 100 of the spoons; and
  b) to angularly tilt member 12 as in FIG. 11 in direction 101 to create an engagement position of edges 12d of the enlargement 12b adjacent opening 12c with the side of the support at which the member 12 is to be frictionally retained in position, due to force exerted by the eyelid upon spoon 14. See FIG. 10.

Accordingly, at least one of the members 12 and 13 has or have adjustable connection to the support to be selectively positioned relative to the other of said members whereby the spoons may be relatively adjustably spread positioned.

FIGS. 3 and 4 show an elongated guide groove 35 at the underside of the support 11 to receive a tang 35a projecting from 12b, for longitudinally guiding travel of member 12.

FIGS. 5-11 show details of the members 12 and 13 as related to support or strut 11.

FIG. 12 shows an alternative support or strut 11' having rack teeth 37 spaced along its length for engagement by edges 12d of member 12, as 12 is tilted, as seen in FIG. 11.

In the above, member 12 may be considered a first frame; and member 13 and support 11, may be considered as a second frame. Spoons 14 and 15 may be considered as eyelid retractors.

FIG. 13 shows a tray 50 carrying two sets of such frames, in a container 51, having pockets 52 in transparent tray wall 53, to receive the frames.

Eyelid depressors 54 are also shown as carried in wall 53 pocket 55. Such depressors and the specula consist of medical grade materials.

We claim:

1. An eyelid speculum comprising
   a) a longitudinally elongated support,
   b) first and second elongated members carried by the support to extend laterally, and eyelid positioning spoons carried by said members,
   c) at least one of the members having adjustable connection to the support to be selectively positioned relative to the other of said members whereby the spoons may be relatively adjustably positioned,
   d) and wherein handles are located at opposite ends of the support, the members having end portions located between the handles,
   e) there being interengagement surfaces on the one member and on the support providing for limited rocking of the one member relative to the support, said surfaces relatively slidable, and which have positions in which edges defined by the members forcibly engage to limit rocking of spoons when engaging the eyelids, selective rocking of said one member toward and away from the other member, being operable to adjust the relative positioning of said spoons
   f) wherein said interengagement surfaces on the support and on said one member are smooth and free of rack teeth, and
   g) wherein the interengagement surfaces are configured to be relatively tiled by the eyelids to engage and block travel of the one member along the support.

2. The speculum of claim 1 wherein the one member defines a through opening proximate one end thereof, and the support extends through said opening.

3. The speculum of claim 2 wherein said opening has a substantially rectangular cross section.

4. The speculum of claim 3 wherein the support has a substantially rectangular external cross section.

5. The speculum of claim 4 including guide means on the support and on said one member to guide travel of said one member along the support, and wherein said guide means intersects both of said rectangular cross sections.

6. The speculum of claim 5 wherein said cross sections loosely interfit.

7. The speculum of claim 4 wherein said cross sections loosely interfit.

8. The speculum of claim 1 wherein said one member has an end portion which is adjustably shiftable along the support.

9. The speculum of claim 8 wherein said end portion forms a through opening to pass said support and define therewith a loose adjustable connection.

10. A combination comprising the speculum of claim 1 and a tray having intersecting pockets receiving the support, and said members, in spaced appart exposed relation.

11. The combination of claim 10 including depressors and wherein said tray, specula and depressors consist of medical grade material.

12. The speculum of claim 1 wherein said interengagement surfaces on the support define a rack with said surfaces thereof spaced along lengthwise extent of the support.

13. The speculum of claim 1 wherein the interengagement surfaces on the support and on said one member block travel of the one member along the support.

14. A combination comprising the speculum of claim 1 and a tray having intersection pockets receiving the support, and said members.

15. The speculum of claim 1 including guide means on the support and on said one member to guide travel of said one member along the support.

* * * * *